United States Patent [19]

Schlegel

[11] 4,424,597
[45] Jan. 10, 1984

[54] POSTERIOR CHAMBER IMPLANT LENS

[75] Inventor: Hans-Joachim Schlegel, Bad Homburg, Fed. Rep. of Germany

[73] Assignee: Inprohold Establishment, Vaduz, Liechtenstein

[21] Appl. No.: 374,439

[22] Filed: May 3, 1982

[30] Foreign Application Priority Data

May 13, 1981 [DE] Fed. Rep. of Germany ....... 3119002

[51] Int. Cl.³ .......................... A61F 1/16; A61F 1/24
[52] U.S. Cl. .......................................................... 3/13
[58] Field of Search .......................................... 3/13, 1

[56] References Cited

U.S. PATENT DOCUMENTS

| | | | |
|---|---|---|---|
| 3,866,249 | 2/1975 | Flom | 3/13 |
| 4,110,848 | 9/1978 | Jensen | 3/13 |
| 4,172,297 | 10/1979 | Schlegel | 3/13 |
| 4,242,762 | 1/1981 | Tennant | 3/13 |
| 4,254,510 | 3/1981 | Tennant | 3/13 |
| 4,298,994 | 11/1981 | Clayman | 3/13 |

FOREIGN PATENT DOCUMENTS 2717706 10/1978 Fed. Rep. of Germany ............ 3/13

*Primary Examiner*—Ronald L. Frinks
*Attorney, Agent, or Firm*—Erwin S. Teltscher

[57] ABSTRACT

A posterior chamber implant lens as a replacement for the natural lens surgically removed, in particular extracapsularly, from the eye of a living being of a higher order, with a central lens body and holding means arranged on the lens body, extending radially outwards from the periphery of the body and fixing it in its position, of a homogeneous, clear, vulcanized silicone rubber, wherein (a) the lens body is formed as a convex lens, wherein the rear surface facing the rear wall of the lens capsule has a greater, preferably much greater curvature than the front surface facing the iris, (b) a basically radially outwardly extending, thin-walled support which encircles the center point of the lens body and has a diameter of between approx. 9.0 and approx. 12.0 mm, preferably of about 10.0 to 11.0 mm (c) there are several openings in the support element distributed over the element, preferably in the form of round holes (d) the support element has a material thickness of between approx. 0.15 mm and 0.40 mm, preferably of about 0.20 mm to 0.25 mm (e) there is preferably situated an outwardly rounded-off ridge on at least a part of the outer edge of the support element (f) the vulcanized silicone material (organopolysiloxane) has a specific gravity between 1.01 and 1.08 preferably of about 1.02

(g) the vulcanized silicone material has a Shore hardness between about 30 and 60, preferably of about 40 to 50, and (h) the vulcanized silicone material has a temperature resistance, without deformation of the lens and its components of over 356° F. during a longer dry heat treatment lasting at least 100 hours.

13 Claims, 5 Drawing Figures

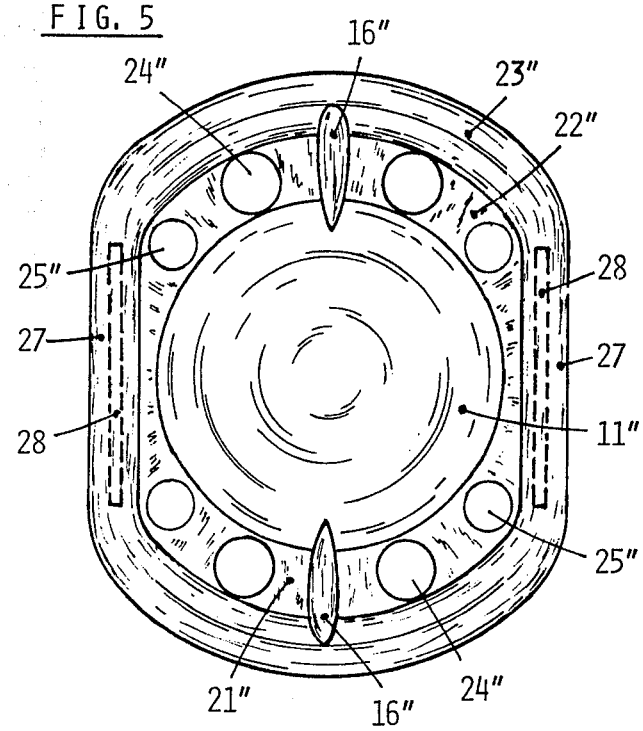

POSTERIOR CHAMBER IMPLANT LENS

BACKGROUND OF THE INVENTION

The invention relates to a posterior chamber implant lens of a homogeneous, clear synthetic material, acting as a replacement for the natural lens surgically removed, in particular extracapsularly, from the eye of a living being of a higher order, which (a) has a central lens body and (b) has holding means on the lens body extending radially outwards from its periphery and fixing it in its position, being of a homogeneous, clear, vulcanized silicone rubber.

Some time past (1949), Ridley in England, attempted to replace extracapsularly removed eye lenses with artificial acrylic glass lenses implanted in the posterior chamber of the eye. However, these attempts more or less failed due to various reasons, inparticularly due to reasons of insufficiently formed lenses and poor material, as well as due to insufficient sterilization, and for this reason a change was made to implant lenses of polymethyl methacrylate (PMMA) which consist of a planoconvex disk on which holding means or support elements of various types are attached, in the anterior chamber of the eye of living beings, in particular human beings, in front of the iris. However, this method also did not bring striking success, and for this reason, in recent years, the lenses of the type in question were attached to the iris with wire or plastic side pieces and possibly sewn onto the iris.

Apart from PMMA, polyamides were also used as material for such lenses. The disadvantage of these materials lies in particular in the fact that the lenses made out of them cannot be surgically perfectly sterilized. None of the hitherto conventionally used implant lenses can stand up to the heat sterilization by means of overheated steam or hot air, which must be used in order to reach a correct, germ-free sterilization (including bacteria spores).

Accordingly, surgery was forced to make do with subjecting the implant lenses to a chemical liquid degermination, i.e. virtually disinfecting them immediately after production, and then preserving them in more or less suitable liquids in ampoulated form. The lenses are removed from these ampoules immediately before the operation. The limitations of such a chemical liquid degermination lie in the present case in their not being able to destroy bacteria spores, furthermore, these—not indifferent—chemicals easily accumulate in plastic bodies within the eye in an uncontrolled manner and over a longer length of time, due to an exponential function. This material behavior gives cause for concern, particularly for an eye implant.

Through the DE-AS No. 26 07 462 an implant lens became known based on the same inventor. This lens is to be attached to the iris and is to be made of a very particular silicone rubber. The suggestion of selecting this plastic material had the important advantage that the lenses could, for the first time, be sterilized using steam or hot air with the sufficiently high temperatures.

Implant lenses of the first generation, after Ridley placed his acrylic glass lens in the posterior chamber of the eye or in the lens capsule, were lenses of this aforementioned type. As a result of the then soon occurring, considerable complications, there was a change to implanting anterior chamber lenses which were formed with the most various of structures. However, also these lenses which were described as those of the second generation, did not bring about a solution to the prevailing problems.

Lenses of the third generation was the name given to those lenses which were attached to the iris by means of their holding means arranged on them. The technology for implanting such lenses has been refined and improved. However they are still burdened with the disadvantage that they are made of PMMA or other materials which, seen in a physiological aspect, still encounter a certain amount of risk.

A further disadvantage of these lenses, as also is the case with the anterior chamber lenses, is that, seen from the optical system of the eye, the lens is not lying in a favorable position. The posterior chamber lenses, thus recommended for this reason have however not been able to prove themselves convincingly, on the one hand due to their form and on the other hand due to the material of which they are made.

SUMMARY OF THE INVENTION

The invention has as its object to provide a posterior chamber implant lens which avoids those negative complications which have occurred with the hitherto used lenses, on the one hand due to its form and structure, on the other hand due to the specifically used material. The lens to be made should have as great a mechanical stability as possible with low, optimum specific gravity of the material, corresponding approximately to that of the aqueous humor or marginally greater than this value. The lens, which becomes practically weightless as a result of the hydrostatic lift, gives rise to a very, very slight mechanical tissue strain on the surrounding tissue, if any at all.

Furthermore, the lens to be provided is to have a suitable elasticity which is not only of advantage for the implanting of the lens. As a result of its form, the anatomic lens position is assured. However where surface pressure can occur on sensitive tissue parts, this should be kept as low as possible.

It is a further object of the invention that the lens should be free from any inner mechanical stresses. Furthermore its material should be such that impairment of the lens surface during subsequent surgery, which will occasionally be necessary, does not have any detrimental influence on the dioptrical properties of the lens. Finally, the posterior chamber implant lens advantageously of one-piece design, should be physiologically compatible, chemically stable and physically clear and be able to be subjected to sterilization at temperatures in the range of 392° F.

A lens fulfilling these requirements is a posterior chamber lens formed according to the invention which has the features listed below in combination with each other:

1. The lens body is formed as a convex lens wherein the rear surface facing the lens capsule rear wall has a greater, preferably much greater curvature that the front surface facing the iris;

2. on the lens body is situated a thin-walled support element extending basically radially outwards, the outer edge of which encircles the center point of the lens body and has a diameter between approx. 9.0 and approx 12.0 mm, preferably about 10.0 to 11.0 mm;

3. in the support element are positioned several openings distributed over the element, preferably in the form of round holes;

4. The support element has a material thickness between about 0.15 mm and 0.40 mm, preferably about 0.20 mm to 0.25 mm;

5. on at least a part of the outer edge of the support element is preferably situated an outwardly rounded-off ridge;

6. the vulcanized silicone material (organopolysiloxane) has a specific gravity of between 1.01 and 1.08 preferably of about 1.02;

7. the vulcanized silicone material has a Shore hardness of between about 30 to 60, preferably of about 40 to 50;

8. the vulcanized silicone material has a temperature resistance without deformation of the lens and its components, of over 356° F. during a longer, dry heat treatment lasting at least 100 hours;

A so formed posterior chamber implant lens makes it possible to functionally fully replace the particularly extracapsularly removed clouded contents of the lens, at an optically favorable position, wherein it simultaneously serves as mechanically stable dividing or supporting wall towards the vitreous body of the eye. As successful experiments have shown, after the making of a circular incision in the capsule front wall and after subsequent removal of the contents of the lens, the artificial lens can be either placed in the remaining capsule sack, completely or partly, or it can also be placed in the posterior chamber, i.e. between the lens capsule and the iris, wherein it supports itself with its outer periphery in the ciliary groove.

Further features and advantageous formations of the posterior chamber implant lens constructed according to the invention can be seen from the dependent claims as well as from the following description of preferred embodiments.

BRIEF DESCRIPTION OF THE DRAWINGS

FIG. 5 is a view of a posterior chamber implant lens as a third embodiment.

DETAILED DESCRIPTION OF THE DRAWINGS

Figure 1:
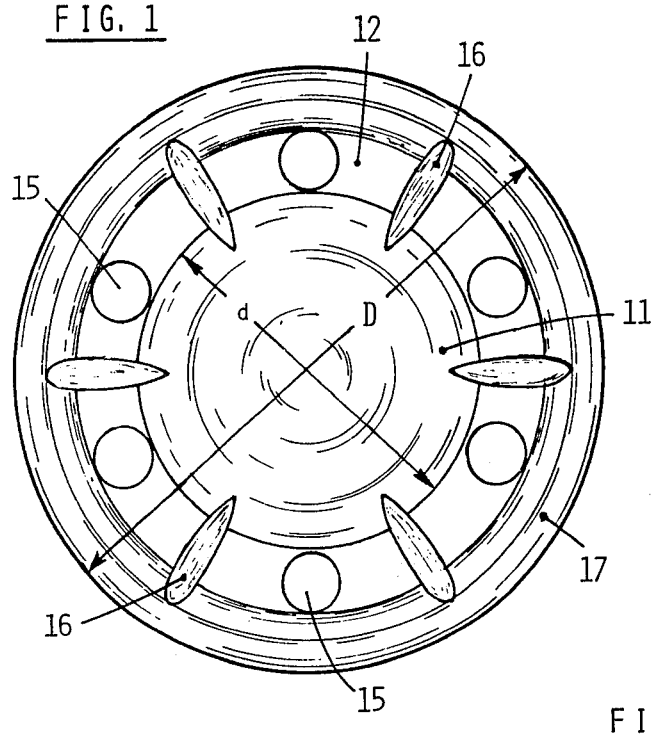
FIG. 1 is a view of a posterior chamber implant lens formed according to the invention as a first embodiment.

As is shown in FIG. 1, the central lens body 11 which has a diameter d of preferably about 5.5 to 6.0 mm is surrounded by an outwardly extending support element ring 12 with which the implant lens supports itself against the in particular peripherally bordering tissue in the eye. The support element 12 has a bend towards the rear wall of the lens capsule so that the center plane of the lens body 11 is displaced towards the plane in which the outer edge of the support ring 12 is situated by about 0.5 mm to 2 mm. As particularly shown in FIG. 2, the rear surface 13 of the lens 11 facing the lens capsule has a greater curvature than the front surface 14 of the lens. On the one hand this corresponds to the form of the natural lens of the eye and on the other hand the severe bulging of the lens body 11 to the rear gives a better tension of the lens capsule rear wall than would be the case if the bulging of the rear surface of the lens body 11 were less. The radius of curvature $r_1$ of the front surface 14 of the lens body 11 is about 1.6 to 2.2 times greater than the radius of curvature $r_2$ of the rear surface 13. The lens body has a diameter (d) of about 4.0–6.5 mm, preferably 5.5 to 6 mm.

In the support ring 12 surrounding the lens body 11, are situated openings in the form of round holes 15 which can be evenly or unevenly arranged over the element, having the task of letting aqueous humor pass through. If desired, and if expedient, reinforcement ribs 16 can be arranged on the support ring 12, which simultaneously serve to keep off adjacent tissue from the surface of the support ring 12, in particular in the area of the holes 15.

On the outer edge of the support ring 12 a ridge 17 can be arranged over the entire periphery or just over a part of it, said ridge effecting a considerable reduction in the surface pressure acting of the supporting tissue, inparticularly then when the implant lens is placed in the posterior chamber in such a way that it supports itself with its edge in the ciliary groove. The thickness of the ridge 17 is about 1.5 to 3.0 times as great as the thickness of the support ring itself.

Figure 2:
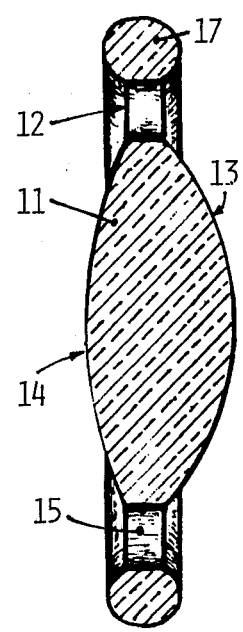
FIG. 2 is a cross section through the lens according to FIG. 1.
Figure 3:
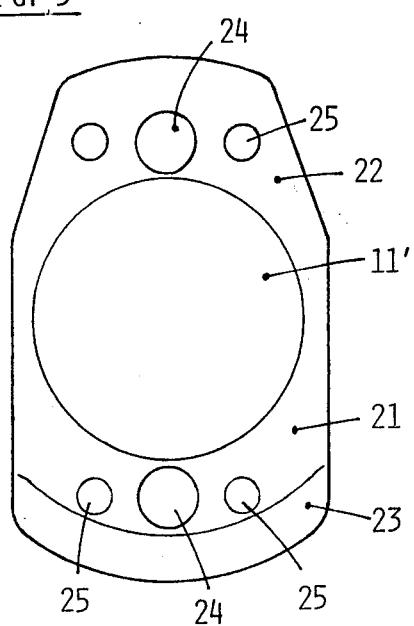
FIG. 3 is a view of a posterior chamber implant lens as a second embodiment.

With the embodiment according to FIG. 3, which principally has the same structure as that of FIG. 1 and 2, two diametrically opposing support flaps 21, 22 are arranged on the central lens body 11' which correspond to the support ring 12 of the first embodiment. The width of these support flaps 21, 22 corresponds approx. to the diameter d of the central lens body 11' or is slightly greater than it. On the edge of the lower support flap 21 and possibly on the edge of the upper support flap 22 an annular ridge 23 can be arranged respectively. Between these and the central lens body 11' are openings in the form of round holes 24, 25. The larger holes 24 have a diameter of about 1 to max. 2 mm, the smaller holes 25 have a diameter of about 0.5 to 0.7 mm. These holes have on the one hand the already mentioned task, and on the other hand they have the effect that the support flaps 21, 22 tend to bend more easily in the cross direction, which is particularly advantageous during the implantation when the lens is to be placed in the opened and emptied lens capsule. Depending on the desired conditions, several larger or smaller openings can be made in the support flaps 21, 22.

Advantageously, the upper support flap 22 can slightly taper towards its outer edge, this being of particular advantage if such a lens is to be planted in the lens capsule, as in this case the edge of the capsule front wall opening which is cut in order to remove the lens fibers, can be more easily pulled over the upper support flap 22. In the case of the lenses placed inside the lens capsule, the openings in the support flaps 21, 22 have a further advantage that either remaining or ongrowing lens fibers anchor themselves in the openings and thus contribute to a further fixing of the lens.

Figure 4:
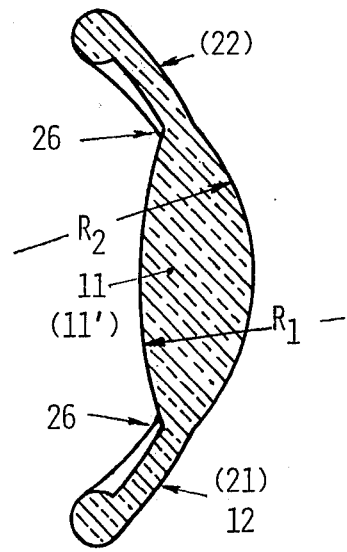
FIG. 4 is a cross section through a variation of the lens according to FIG. 1 or FIG. 3

As can be seen from FIG. 4, the support ring 12 or the support flaps 21, 22, can have a bend 26 or a greater or smaller degree of inclination towards the inner of the eyeball in order to enable the rear surface 13 of the lens body 11 coming to rest further in i.e. towards the center point of the eyeball, this meaning an even greater tensioning of the lens capsule rear wall. Expediently, a radius $R_2$, optimum in this aspect, is chosen for the rear lens surface, which is then left the same size for all implant lenses, and in connection with the desired refractive power, merely the radius $R_1$ of the front lens surface is altered.

As already mentioned, the implant lens placed in the lens capsule, or in front of the lens capsule, supports the vitreous body from the front instead of the natural lens. In order to be able to fulfil this task even better, especially then when the support elements of the lens body are relatively thin-walled, FIG. 5 shows stiffening or reinforcement ribs or ridges 27 which can be arranged on the lateral edges of the support flaps 21", 22" provided with the holes 24" and 25", which generally give the lens more rigidity. Also, for the same purpose, stiffening ribs 16" can be arranged between the lens body 11" and the edge ridges 23".

If necessary, additional stiffening elements can be furthermore embedded in the stiffening ribs or reinforcement ribs or ridges 27, such as, inparticular, wire pieces 28.

What is claimed is:

1. Posterior chamber implant lens as a replacement for the natural lens surgically removed, in particular extracapsularly, from the eye of a living being of a higher order, which has a central lens body, and holding means arranged on said lens body extending radially outwards from the periphery for fixing said lens body in its position, said lens comprising a homogeneous, clear, vulcanized silicone rubber which has the following features in combination with each other:
   (a) the lens body is formed as a convex lens, wherein the rear surface for facing the lens capsule rear wall has a greater, preferably much greater curvature than the front surface facing the iris;
   (b) on the lens body is situated a basically radially outwardly extending, thin-walled support element, the outer edge of which encircles the center point of the lens body with a diameter (D) of between approx. 9.0 and approx 12.0 mm, preferably about 10.0 to 11.0 mm;
   (c) in the support element are several spaces distributed over the element, preferably in the form of round holes;
   (d) the support element has a material thickness of between about 0.15 mm and 0.40 mm, preferably of about 0.20 mm to 0.25 mm;
   (e) the vulcanized silicone material (organopolysiloxane) has a specific gravity of between 1.01 and 1.08, preferably of about 1.02;
   (f) the vulcanized silicone material has a Shore hardness of between about 30 and 60, preferably of about 40 to 50;
   (g) the vulcanized silicone material has a temperature resistance without deformation of the lens and its components of over 356° F. during a longer, dry heat treatment lasting at least 100 hours.

2. Posterior chamber implant lens according to claim 1, wherein on at least a part of the outer edge of the support element there is positioned an outwardly rounded-off ridge.

3. Posterior chamber implant lens according to claim 1, wherein the support element for the central lens body comprises a support ring surrounding said lens body.

4. Posterior chamber implant lens according to claim 1, wherein the support element for the central lens body comprises two support flaps extending from the periphery outwards from said lens body and in opposite directions to each other, being in the vertical direction when in the position of implantation, the width of which corresponds approximately to the diameter (d) of the lens body.

5. Posterior chamber implant lens according to claim 4, wherein the spaces in the support element are in two diametrically opposed areas being at least one, however preferably two or three holes respectively.

6. Posterior chamber implant lens according to claim 1, wherein the support element has a bend towards the lens capsule rear wall being such that the center plane of the lens body is displaced towards the plane in which the outer edge of the support ring or the support element are situated by about 0.5 to 2 mm.

7. Posterior chamber implant lens according to claim 4, wherein the edges of the support flaps are substantially parallel, and wherein on the parallel edges of the support flaps, facing each other, there are arranged stiffening ribs or ridges.

8. Posterior chamber implant lens according to claim 1, wherein in the peripheral edge area of the support element there are arranged stiffening ribs or the like.

9. Posterior chamber implant lens according to claim 1, wherein the lens body has a diameter (d) of about 4.0 to 6.5 mm, preferably of about 5.5 to 6.0 mm.

10. Posterior chamber implant lens according to claim 1, wherein the radius $r_1$ of the front surface of the lens body is about 1.6 to 2.2 times greater than the radius $r_2$ of the rear surface of the lens body.

11. Posterior chamber implant lens according to claim 2, wherein the ridge on the outer edge of the support element is about 1.5 to 3 times as thick as said support element.

12. Posterior chamber implant lens according to claim 5, wherein some spaces or holes are larger than others, and wherein the larger spaces or holes in the support element have a diameter of about 1.0 mm to 2.0 mm and the smaller spaces or holes have a diameter of about 0.5 mm to 0.7 mm.

13. Posterior chamber implant lens according to claim 5, wherein the width of the upper support flap is tapered towards the outside.

* * * * *